US011685755B2

(12) United States Patent
Baratta et al.

(10) Patent No.: US 11,685,755 B2
(45) Date of Patent: Jun. 27, 2023

(54) DICARBONYL RUTHENIUM AND OSMIUM CATALYSTS

(71) Applicants: UNIVERSITA DEGLI STUDI DI UDINE, Udine (IT); INNOVATION FACTORY S.R.L., Trieste (IT)

(72) Inventors: Walter Baratta, Udine (IT); Salvatore Baldino, Sassari (IT); Steven Giboulot, Sainte-Maxime (FR); Shuanming Zhang, Jiangsu (CN)

(73) Assignees: Universita' Degli Studi Di Udine, Udine (IT); Innovation Factory S.R.L., Trieste (IT)

( * ) Notice: Subject to any disclaimer, the term of this patent is extended or adjusted under 35 U.S.C. 154(b) by 1267 days.

(21) Appl. No.: 16/075,333

(22) PCT Filed: Feb. 3, 2017

(86) PCT No.: PCT/IB2017/050600
§ 371 (c)(1),
(2) Date: Aug. 3, 2018

(87) PCT Pub. No.: WO2017/134620
PCT Pub. Date: Aug. 10, 2017

(65) Prior Publication Data
US 2021/0107929 A1 Apr. 15, 2021

(30) Foreign Application Priority Data

Feb. 5, 2016 (IT) .................... 102016000011936

(51) Int. Cl.
*C07F 15/00* (2006.01)
*B01J 31/16* (2006.01)

(52) U.S. Cl.
CPC ....... *C07F 15/0046* (2013.01); *B01J 31/1616* (2013.01)

(58) Field of Classification Search
None
See application file for complete search history.

(56) References Cited

FOREIGN PATENT DOCUMENTS

| EP | 0773064 A1 | 5/1997 |
|---|---|---|
| JP | H7-500630 A | 1/1995 |
| JP | H9-262477 A | 10/1997 |
| WO | 9404497 | 3/1994 |
| WO | WO 2005/051965 A2 | 6/2005 |
| WO | 2011048727 A | 3/2013 |

OTHER PUBLICATIONS

Baratta et al. Organometallics 2004, 6264-6272.*
Joshi et al., "Bis(dipyridophenazine)(2-(2'-pyridyl) pyrimidine-4-carboxylic acid)ruthenium(II) Hexafluorophosphate: A Lesson in Stubbornness", ChemMedChem, 2014 vol. 9, No. 7, pp. 1419-1427.
Spiccia, et al., "Synthetic routes to homoleptic and heteroleptic ruthenium (II) complexes Incorporating bidentate imine ligands", Coordination Chemistry Reviews, 2004, vol. 248, pp. 1329-1431.
Aguirre et al., "Water-gas shift reaction catalyzed by mononuclear ruthenium complexes containing bipyridine and phenanthroline derivatives", Applied Organometallic Chemistry, 2002, pp. 597-600.
Jung et al., "Hydrogenation of trans-Cinnamaldehyde with Hydrido-Carbonyl Osmium(II) Complexes of Chelating Phosphine Ligands", Bull. Korean Chem. Soc. 1997, vol. 18, No. 8, pp. 806-810.
Chelucci, et al., "Ruthenium and Osmium Complexes Containing 2-(aminomethyl)pyridine (Ampy)-based Ligands in Catalysis" Coordination Chemistry Reviews 300; Copyright 2015; pp. 29-85.
Mezzeiti et al., "Novel Ruthenium (II) Complexes with the Atropoisomeric Diphosphine 2,2-Dimethyl-6,6-bis(diphenylphosphino)biphenyl", Gazzetta Chimica Italiana, 123, 1993, 155-164.
Popov et al., Zhumal Obshchei Khimii / Zh. Obshch. Khim., 1988, 58(5), 1172-1173 (Year 1988).
W.Baratta et al., "RuCl2[(2,6-Me2C6H3)PPh2]2: A New Precursor for Cyclometalated Ruthenium(II) Complexes," Organometallics 2004 (published on web Nov. 16, 2004), 23 (26), 6264-6272.
W.Baratta et al., "Cyclometalated Ruthenium(II) Complexes as Highly Active Transfer Hydrogenation Catalysts," Agnew. Chem. Int, Ed, Jul. 5, 2004 (first published Jun. 29, 2004), 43, 3584-3588.
Bera et al., "Dynamics of H-atom Exchange in Stable cis-dihydrogen/hydride Complexes of Ruthenium(II) Bearing Phosphine and N—N Bidentate Ligands," Dalton Transactions: The International Journal for Inorganic, Organometallic and Bioinorganic Chemistry, vol. 43, No. 12, Jan. 1, 2014, p. 4726-4733.
Cavarzan et al., "Neutral and Cationic Ruthenium Carbonyl Complexes [Ru(CO)(2.2'-dipyridylamine)(PR3)Cl2] and [Ru (CO)(N—N)(PPh3)2(H)]Cl: Synthesis, Structural, Characterization and Transfer-Hydrogenation," Transition Metal Chemistry, vol. 40, No. 1, Oct. 31, 2014, pp. 117-123.
Caravan et al., "Mixed Phosphine/Diimines and/or Amines Ruthenium Carbonyl Complexes: Synthesis, Characterization and Transfer-Hydrogenation," Polyhedron vol. 62, Oct. 7, 2013, pp. 75-82.
Kumar et al., "Synthesis and Characterization of Ruthenium(II) Complexes Based on Diphenyl-2-Pyridylphosphine and Their Applications in Transfer Hydrogenation of Ketones," Inorganica Chimica Acta, vol. 368, No. 1, Dec. 21, 2010, pp. 124-131.
Kamatchi et al., "Influence of Carboxylic Acid Functionalities in Ruthenium(II) polypyridyl complexes on DNA binding, cytotoxicity and antioxidant activity: Synthesis, structure and in vitro anticancer activity", European Journal of Medicinal Chemistry, vol. 59, Jan. 1, 2013, pp. 253-264.

(Continued)

*Primary Examiner* — Clinton A Brooks
(74) *Attorney, Agent, or Firm* — Baker Hostetler

(57) ABSTRACT

The disclosure relates to dicarbonyl complexes of ruthenium and osmium with bi- and tridentate nitrogen and phosphine ligands. The disclosure relates to methods for preparing these complexes and the use of these complexes, isolated or prepared in situ, as catalysts for reduction reactions of ketones and aldehydes both via transfer hydrogenation or hydrogenation with hydrogen.

20 Claims, No Drawings

(56) References Cited

OTHER PUBLICATIONS

Peter John, "Strukturbestimmung Isomerer Rutheniumverbindungen des Typs Ru(CO)2L2X2 durch Infrarot (uCO)—und Dipolmoment-Messungen," Chemische Berichte, vol. 103, No. 7, pp. 2178-2196, Jan. 13, 1970.
Moreno M.A. et al., "Synthesis, Characterization, Reactivity and Theoretical Studies of Ruthenium Carbonyl Complexes Containing Ortho-Substituted Triphenyl Phosphanes," Journal of Organometallic Chemistry, vol. 690, No. 16, pp. 3803-3814, Aug. 15, 2005.
Zhang et al., "Synthesis of [RuX(CO)(dppp)(NN)]Cl (X=H, Cl; NN=en, ampy) Complexes and Their Use as Catalysts for Transfer Hydrogenation" Organometallics 2013, 32(19), 5299-5304.
PCT/IB2017_050600 International Search Report dated Mar. 17, 2017.
PCT/IB2017_050600 Written Opinion dated Mar. 17, 2017.
Registry No. 154293-50-2, Chemical Library, CA, CAPLUS, Apr. 12, 1994, 1 page.
Registry No. 142562-82-1, Chemical Library, CA, CAPLUS, CASREACT, Jul. 24, 1992, 1 page.
Registry No. 90981-42-3, Chemical Library, CA, CAPLUS, Nov. 16, 1984, 1 page.
Registry No. 90893-62-2, Chemical Library, CA, CAPLUS, Nov. 16, 1984, 1 page.
Registry No. 857253-17-9, Chemical Library, CA, CAPLUS, CASREACT, Jul. 27, 2005, 1 page.
Registry No. 857253-16-8, Chemical Library, CA, CAPLUS, CASREACT, Jul. 27, 2005, 1 page.
Registry No. 187406-32-2, Chemical Library, CA, CAPLUS, CASREACT, Mar. 21, 1997, 1 page.
Registry No. 180787-56-8, Chemical Library, CA, CAPLUS, Sep. 13, 1996, 1 page.
Registry No. 175234-94-3, Chemical Library, CA, CAPLUS, CASREACT, TOXCENTER, Apr. 17, 1996, 1 page.
Registry No. 954103-55-0, Chemical Library, CA, CAPLUS, CASREACT, Nov. 16, 2007, 1 page.

* cited by examiner

DICARBONYL RUTHENIUM AND OSMIUM CATALYSTS

CROSS-REFERENCE TO RELATED APPLICATIONS

This application is the National Stage of International Patent Application No. PCT/162017/050600, filed Feb. 3, 2017 which claims priority from Italian Patent Application No. 102016000011936, filed Feb. 5, 2016, the disclosures of each of which are incorporated herein by reference in their entireties for any and all purposes.

The disclosure relates to dicarbonyl complexes of ruthenium and osmium with bi- and tridentate nitrogen and phosphine ligands. The disclosure relates to methods for preparing these complexes and the use of these complexes, isolated or prepared in situ, as catalysts for reduction reactions of ketones and aldehydes both via transfer hydrogenation or hydrogenation with hydrogen.

STATE OF THE ART

The carbonyl compounds (aldehydes and ketones) can be easily reduced to alcohols by molecular hydrogen (hydrogenation) or donor molecules of hydrogen (transfer hydrogenation) through the use of catalysts based on rhodium, iridium, iron, ruthenium and osmium.

The development of complexes that catalyze the chemo- and stereo-selective reduction of carbonyl compounds is a subject of considerable academic and industrial interest, a target which can be achieved through the fine-tuning of the ligands of the complexes. The hydrogenation, which entails the use of hydrogen under pressure, is an industrial process for the synthesis of alcohols. A significant breakthrough for the development and application of this process was given in the late '90s by a new class of ruthenium complexes of formula $RuCl_2(P)_2$(diamine) and $RuCl_2(PP)$ (diamine) (P=phosphine and PP=diphosphine) for the catalytic enantioselective hydrogenation of ketones. By using a suitable combination of chiral diphosphine and diamine ligands, these complexes were proven to efficiently catalyze the asymmetric reductions of carbonyl compounds with production of chiral alcohols with high enantiomeric excess.

In addition to hydrogenation, the transfer hydrogenation reaction has also been developed using 2-propanol or formic acid as hydrogen source, with the advantage of employing non-pressure systems and reducing the risk.

In 2004 Baratta and collaborators have developed ruthenium complexes containing phosphines and bi- and tridentate aminopyridine ligands which show high catalytic activity in hydrogenation and transfer hydrogenation.

It is worth pointing out that the dicarbonyl derivative $RuCl_2(CO)_2$(bipy) containing a bidentate nitrogen ligand (L. Spiccia et al., Coord. Chem. Rev. 2004, 248, 1329) shows catalytic activity for several processes, including the epoxidation of olefins, the water gas shift reaction and the photochemical and electrochemical reduction of $CO_2$. The cyclometallated carbonyl derivatives $[RuCl(CN)(CO)_2]_2$ show catalytic activities in the alkyne dimerization reaction and in the oxidation of alcohols to ketones. The interest in these systems stems from the fact that the presence of a Ru—CO bond makes the catalyst more robust and less sensitive to the decarbonylation reactions of the substrates which can deactivate the catalysts, preventing their use in very low quantities.

Moreover, to make the reduction of carbonyl compounds to alcohols economically competitive, via transfer hydrogenation or hydrogenation, the development of catalysts with high chemo- and stereo-selectivity is a crucial issue.

Furthermore, the catalysts have to display high productivity and should be easily prepared from commercially available starting material through simple and safe synthetic routes.

The purpose of the present invention relates to the synthesis of complexes of ruthenium and osmium containing two CO ligands in combination with bidentate and tridentate nitrogen ligands and phosphorus-containing ligands. These complexes can be used as catalysts in the reduction of carbonyl compounds by transfer hydrogenation or hydrogenation with molecular hydrogen.

A further object of the present invention is to obtain ruthenium (II) and osmium (II) complexes which can be generated in situ during the reduction of carbonyl compounds or by transfer hydrogenation or hydrogenation with molecular hydrogen.

SUMMARY OF THE INVENTION

In order to achieve the purposes mentioned above, the inventors have identified in a series of dicarbonyl complexes of ruthenium and osmium, containing nitrogen and phosphine ligands, the solution for obtaining catalysts of high catalytic activity in hydrogenation reactions with molecular hydrogen and transfer hydrogenation of carbonyl compounds to alcohols.

Accordingly, the present disclosure refers to a hexacoordinate complex of formula (1):

wherein:

M=Ru or Os;

X and Y are independently selected among halides, hydride, C1-C20 carboxylates and C1-C20 alkoxides;

W is selected among halides, C1-C20 carboxylates and C1-C20 alkoxides;

L is a nitrogen-containing ligand selected among:

(I) a (NN) compound of formula Ia-Ic:

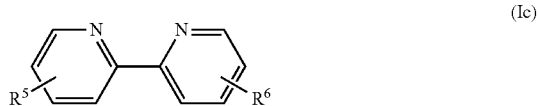

(II) a (HCNN) compound of formula IIa-IIb:

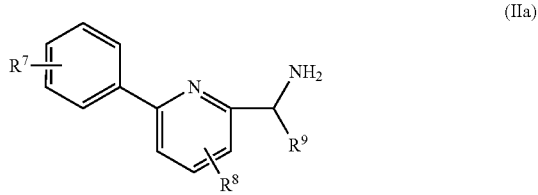

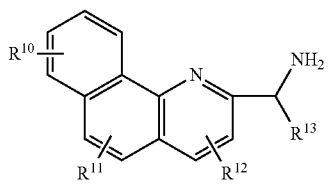

(IIb)

(III) a (CNN) ligand of formula IIc-IId:

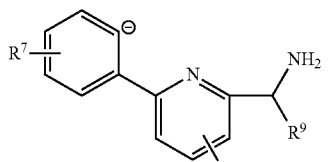

(IIc)

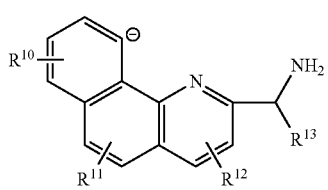

(IId)

wherein $R^1$-$R^{13}$ are independently selected among H, C1-C20 aliphatic groups and C5-C20 aromatic groups; and L' is at least one phosphorus-containing ligand selected among a HCP compound of formula (IVa) and a CP ligand of formula (IVb)

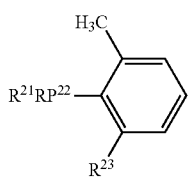

(IVa)

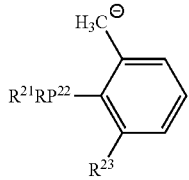

(IVb)

wherein
$R^{21}$-$R^{23}$ are independently selected among H, C1-C20 aliphatic groups and C5-C20 aromatic groups;
and wherein
a, b, c and e are independently 0 or 1;
d is 0, 1 or 2; and
provided that when M is Ru and
a=b=1; c=e=0; d=2 and X=Y=Cl, R23 is not hydrogen;
a=1; b=c=e=0; d=2 and X=Cl, HCP is not (2,6-dimethylphenyl) diphenylphosphine (Hdmpp) and CP is not the anion of (2,6-dimethylphenyl) diphenylphosphine (dmpp); and
a=b=c=1; d=e=0 and X=Y=Cl, L is not ethylenediamine or bipyridine.

In a further aspect, the present disclosure refers to a process to obtain the complex of formula (1) comprising:
(i) reacting a compound of formula $MX_2Y$, wherein M, X and Y are as defined above, with HCOOH, thereby obtaining an intermediate compound of formula $[MXY(CO)_2]_n$;
(ii) reacting the compound of formula $[MXY(CO)_2]_n$, with at least one ligand selected among:
a (HCNN) compound of formula IIa-IIb:

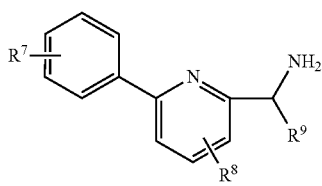

(IIa)

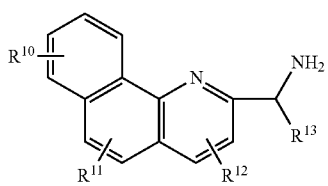

(IIb)

a HCP compound of formula (IVa)

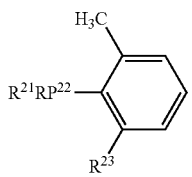

(IVa)

wherein
$R^7$-$R^{13}$ and $R^{21}$-$R^{23}$ are independently selected among H, C1-C20 aliphatic groups and C5-C20 aromatic groups
in the presence of a solvent and optionally of a tertiary amine of formula $N(R^{24}R^{25}R^{26})$, wherein $R^{24}$, $R^{25}$ and $R^{26}$ are independently selected among C1-C6 aliphatic groups; and (iii) optionally reacting the compound obtained in step (ii) with a basic compound selected among potassium carbonate, calcium carbonate and mixtures thereof and/or a nitrogen-containing (NN) compound of formula Ia-Ic:

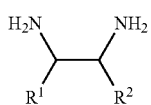

(Ia)

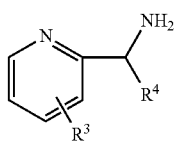

(Ib)

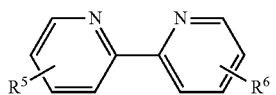

(Ic)

wherein $R^1$-$R^6$ are independently selected among H, C1-C20 aliphatic groups and C5-C20 aromatic groups.

In a further aspect, the present disclosure refers to the use of said ruthenium or osmium complexes as catalysts or pre-catalyst for the reduction reaction of ketones or aldehydes to alcohols by transfer hydrogenation or hydrogenation with molecular hydrogen.

This and other aspects as well as the characteristics and advantages of the present invention will be more apparent from the detailed description below and by the preferred embodiments given as non-limiting illustrations of the invention itself.

DESCRIPTION OF THE INVENTION

As used therein, "aliphatic group" refers to acyclic or cyclic, linear or branched, saturated or unsaturated hydrocarbon, excluding aromatic groups.

As used therein, "substituted aliphatic group" refers to an aliphatic group in which at least one hydrogen atom is replaced by at least one substituent group selected among —OR, —NRR', —NRCOR', —NO₂, —NH₂, —COR, —COOR, —CONRR' and halides, wherein R and R' are equal or different and can be a H or a C1-C20 aliphatic or aromatic group.

As used therein, "aromatic group" also includes substituted aromatic groups and heteroaromatic groups.

As used therein, "substituted aromatic group" refers to aromatic groups in which at least one aromatic hydrogen atom is replaced with at least one substituent group selected among —R, —OR, —NRR', —NRCOR', —NO₂, —NH₂, —COR, —COOR, —CONRR' and halides, wherein R and R' are equal or different and can be a H or a C1-C20 aliphatic or aromatic group.

As used therein, "heteroaromatic group" refers to aromatic groups in which at least one carbon atom which is part of the aromatic ring is replaced with one heteroatom selected among N, S, O and P.

As used therein, "hydrogen-donor" refers to a compound that transfers a hydrogen atom to another compound.

As used therein, "(transfer)hydrogenation" refers to hydrogenation with molecular hydrogen or to transfer hydrogenation using a hydrogen donor compound.

In the present description and appended claims the abbreviations listed in Table 1 are used:

TABLE 1

| Abbreviation of the nitrogen and phosphorus ligands | | |
|---|---|---|
| Chemical name | Abbreviation | Structural formula |
| Nitrogen-containing ligand L | | |
| ethylenediamine | en | 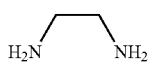 |
| 2-(aminomethyl)pyridine | ampy | 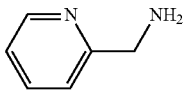 |
| bipyridine | bipy | 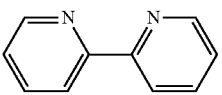 [SMILES: c1ccc(-c2ccccn2)nc1] |
| (1R,2R)-1,2-diphenylethylenediamine | (R,R)-dpen | 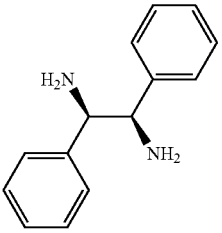 [SMILES: N[C@H](c1ccccc1)[C@H](N)c1ccccc1] |
| (1S,2S)-1,2-diphenylethylenediamine | (S,S)-dpen | 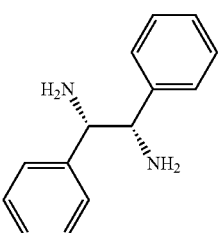 |
| 6-(4-methylphenyl)-2-(aminomethyl)pyridine | Hamtp | 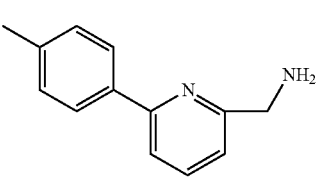 |

TABLE 1-continued

| Abbreviation of the nitrogen and phosphorus ligands | | |
|---|---|---|
| Chemical name | Abbreviation | Structural formula |
| Anionic form of 6-(4-methylphenyl)-2-(aminomethyl)pyridine | amtp | |
| 2-(aminomethyl)benzo[h]quinoline | Hambq | |
| Anionic form of 2-(aminomethyl)benzo[h]quinoline | ambq | |
| 4-phenyl-2-(aminomethyl)benzo[h]quinoline | Hambq$^{Ph}$ | |
| Anionic form of 4-phenyl-2-(aminomethyl)benzo[h]quinoline | ambq$^{Ph}$ | |
| phosphorus-containing ligand L' | | |
| triphenylphosphine | PPh$_3$ | |
| tricyclohexylphosphine | PCy$_3$ | |
| triisopropylphosphine | PiPr$_3$ | |
| 1,3-bis(diphenylphosphino)propane | dppp | |
| 1,4-bis(diphenylphosphino)butane | dppb | |
| 1,1'-bis(diphenylphosphino)ferrocene | dppf | |

TABLE 1-continued

Abbreviation of the nitrogen and phosphorus ligands

| Chemical name | Abbreviation | Structural formula |
| --- | --- | --- |
| (R)-1-[($S_P$)-2-(diphenylphosphino)ferrocenyl-ethyl]diphenylphosphine | (R)-Josiphos | |
| (R)-(+)-2,2'-bis(diphenylphosphino)-1,1'-binaphthalene | (R)-BINAP | |
| (R,R)-Skewphos | (R,R)-BDPP | |
| (2,6-dimethylphenyl)diphenylphosphine | Hdmpp | |
| Anionic form of (2,6-dimethylphenyl)diphenylphosphine | dmpp | |
| (2,6-dimethylphenyl)dicyclohexylphosphine | Hdmppc | |
| Anionic form of (2,6-dimethylphenyl)dicyclohexylphosphine | dmppc | |

The present disclosure refers to a hexacoordinate complex of formula (1):

$$[MX_aY_b(CO)_2L_cL'_d]W_e \quad (1)$$

wherein

M=Ru or Os;

X and Y are independently selected among halides, hydride, C1-C20 carboxylates and C1-C20 alkoxides;

W is selected among halides, C1-C20 carboxylates and C1-C20 alkoxides;

a, b, c and e are independently 0 or 1;

d is 0, 1 or 2;

L is a nitrogen-containing ligand selected among:

(I) a (NN) compound of formula Ia-Ic:

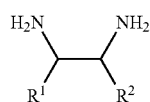
(Ia)

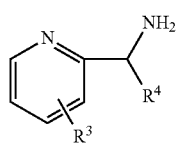
(Ib)

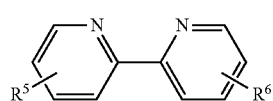
(Ic)

(II) a (HCNN) compound of formula IIa-IIb:

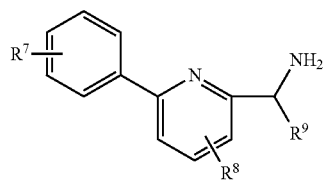
(IIa)

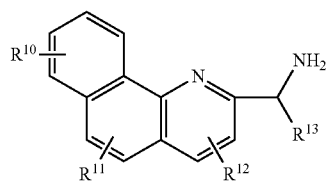
(IIb)

(III) a (CNN) ligand of formula IIc-IId:

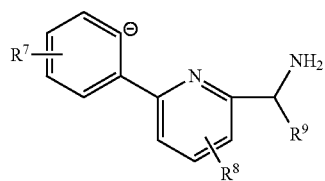
(IIc)

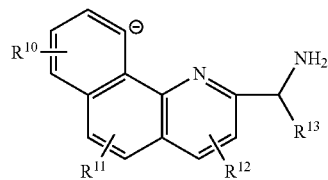
(IId)

wherein $R^1$-$R^{13}$ are independently selected among H, C1-C20 aliphatic groups and C5-C20 aromatic groups, preferably $R^1$ and $R^2$ may be independently selected among H and a phenyl group and/or $R^3$-$R^6$ and $R^8$-$R^{13}$ may be H and/or $R^7$ may be 4-methyl; and L' is at least one phosphorus-containing ligand selected among a HCP compound of formula (IVa) and a CP ligand of formula (IVb)

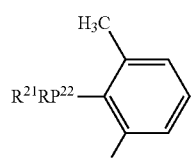
(IVa)

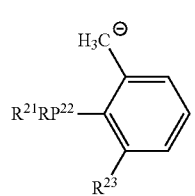
(IVb)

wherein $R^{21}$-$R^{23}$ are independently selected among H, C1-C20 aliphatic groups and C5-C20 aromatic groups, preferably $R^{23}$ may be —$CH_3$ and/or $R^{21}$-$R^{22}$ may be C6-C20 cycloaliphatic group or C6-C20 aromatic group, more preferably $R^{23}$ may be —$CH_3$ and/or $R^{21}$-$R^{22}$ may be independently selected among phenyl and cyclohexyl group;

provided that when M is Ru and a=b=1; c=e=0; d=2 and X=Y=Cl, $R^{23}$ is not hydrogen;

a=1; b=c=e=0; d=2 and X=Cl, HCP is not (2,6-dimethylphenyl) diphenylphosphine (Hdmpp) and CP is not the anion of (2,6-dimethylphenyl) diphenylphosphine (dmpp);

a=b=c=1; d=e=0 and X=Y=Cl, L is not ethylenediamine or bipyridine.

The present disclosure also refers to a process to obtain the complex of formula (1) comprising:

(i) reacting a compound of formula $MX_2Y$, preferably of formula $MX_3$, more preferably of formula $MCl_3$, wherein M, X and Y are as defined above, with HCOOH, thereby obtaining an intermediate compound of formula $[MXY(CO)_2]_n$, preferably of formula $[MX_2(CO)_2]_n$, more preferably of formula $[MCl_2(CO)_2]_n$;

(ii) reacting the compound of formula [MXY(CO)$_2$]$_n$ with at least one ligand selected among:
a (HCNN) compound of formula IIa-IIb:

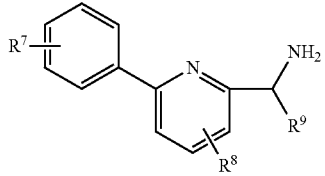

(IIa)

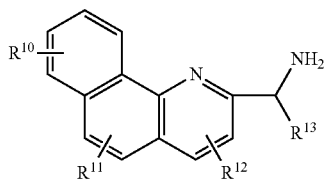

(IIb)

a HCP compound of formula (IVa)

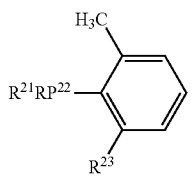

(IVa)

wherein

R$^7$-R$^{13}$ and R$^{21}$-R$^{23}$ are independently selected among H, a C1-C20 aliphatic group and a C5-C20 aromatic group, preferably R$^8$-R$^{13}$ may be H and/or R$^7$ may be 4-methyl and/or R$^{23}$ may be —CH$_3$ and/or R$^{21}$-R$^{22}$ may be C6-C20 cycloaliphatic group or C6-C20 aromatic group, more preferably R$^{23}$ may be —CH$_3$ and/or R$^{21}$-R$^{22}$ may be independently selected among phenyl and cyclohexyl groups, in the presence of a solvent, preferably selected among C1-C6 aliphatic alcohols, more preferably selected among ethanol, methanol or mixtures thereof, and optionally of a tertiary amine of formula N(R$^{24}$R$^{25}$R$^{26}$), wherein R$^{24}$, R$^{25}$ and R$^{26}$ are independently selected among C1-C6 aliphatic group, preferably triethylamine; and (iii) optionally reacting the compound obtained in step (ii) with a basic compound selected among potassium carbonate, calcium carbonate and mixtures thereof and/or a nitrogen-containing (NN) compound of formula Ia-Ic:

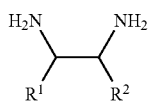

(Ia)

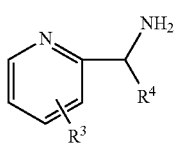

(Ib)

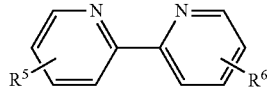

(Ic)

wherein R$^1$-R$^6$ are independently selected among H, C1-C20 aliphatic groups and C5-C20 aromatic groups; preferably, R$^1$ and R$^2$ may be independently selected among H and a phenyl group and/or R$^3$-R$^6$ and R$^8$-R$^{13}$ may be H and/or R$^7$ may be 4-methyl.

After step (iii) the complex of formula (1) may be recovered from the solution by known techniques, such as by precipitation with suitable organic solvents.

The high modularity of the nitrogen-containing ligands (Ia-c) and (IIa-d) in combination with (HCP) and (CP) allows to obtain a large number of well-defined catalysts displaying high chemo- and stereoselectivity.

For the purposes of the present invention, from the combination of the different meanings of M, X, Y, W, L, and L', the complexes of sub-formulas (V)-(IX) given below may be obtained, which are encompassed by the general formula (1).

The ligands of the type HCNN (IIa-b) have the ability to act both as bidentate (IIa-b) or tridentate ligands of the type (IIc-d). In the case of bidentate ligand the coordination occurs through the nitrogen atom of the NH$_2$ group and a second nitrogen atom of the heterocycle.

Thus, according to an embodiment, the present disclosure may refer to a complex of formula (V):

$$MXY(CO)_2(HCNN) \quad (V)$$

wherein M, X, Y and (HCNN) are as defined in formula (1).

The complex of formula (V) containing a HCNN ligand lead to a catalyst with a remarkably higher activity with respect to similar compounds known in the art containing a (NN) ligand.

The present disclosure also refers to a process to obtain complexes of formula (V) comprising:
(i) reacting a compound of formula MX$_2$Y, preferably of formula MX$_3$, more preferably of formula MCl$_3$, wherein M, X and Y are as defined above, with HCOOH, thereby obtaining an intermediate compound of formula [MXY(CO)$_2$]$_n$, preferably of formula [MX$_2$(CO)$_2$]$_n$, more preferably of formula [MCl$_2$(CO)$_2$]$_n$;
(ii) reacting the compound of formula [MXY(CO)$_2$]$_n$ with a (HCNN) compound of formula IIa-IIb:

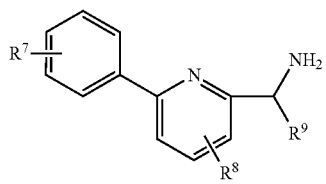

(IIa)

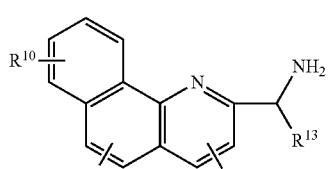

(IIb)

wherein
R[7]-R[13] are independently selected among H, C1-C20 aliphatic groups and C5-C20 aromatic groups, preferably R[7] may be 4-methyl and/or R[8]-R[13] may be H,
in the presence of solvent, preferably selected among a C1-C6 aliphatic alcohol, more preferably selected among ethanol, methanol and mixtures thereof.

Non limiting examples of preferred complexes of formula (V) are:

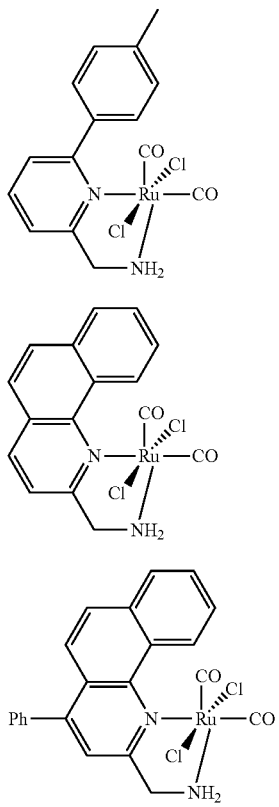

The neutral dicarbonyl complexes 1-3 were obtained by treatment of $[RuCl_2(CO)_2]_n$ polymer (prepared from $RuCl_3 \cdot xH_2O$), with the ligands 6-(4-methylpheny)-2-(aminomethyl)pyridine, 2-(aminomethyl)benzo[h]quinoline and 4-phenyl-2-(aminomethyl)benzo[h]quinoline, respectively, in ethanol.

The HCNN ligands of the type (IIa), which contain a pyridine ring functionalized in the 6 position with an aromatic group, and those of the type (IIb), containing the benzo[h]quinoline system, have the ability to act as anionic tridentate ligands (IIc-IId) through the nitrogen atom of the —$NH_2$ group, a second nitrogen atom of the heterocycle and a cyclometallated carbon atom with the metal.

Thus, according to a further embodiment, the present disclosure may refer to complexes of formula (VI)

$$MX(CO)_2(CNN) \quad (VI)$$

wherein M, X and (CNN) are as defined in formula (1).

The present disclosure also refers to a process to obtain complexes of formula (VI) by:
(i) reacting a compound of formula $MX_2Y$, preferably of formula $MX_3$, more preferably of formula $MCl_3$, wherein M, X and Y are as defined above, with HCOOH, thereby obtaining an intermediate compound of formula $[MXY(CO)_2]_n$, preferably of formula $[MX_2(CO)_2]_n$, more preferably of formula $[MCl_2(CO)_2]_n$;
(ii) reacting the compound of formula $[MXY(CO)_2]_n$ with a (HCNN) compound of formula IIa-IIb:

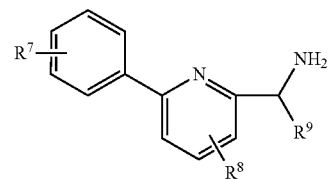

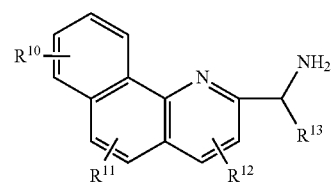

wherein
R[7]-R[13] are independently selected among H, C1-C20 aliphatic groups and C5-C20 aromatic groups, preferably R[7] may be 4-methyl and/or R[8]-R[13] may be H,
in the presence of a solvent, preferably selected among C1-C6 aliphatic alcohols, more preferably selected among ethanol, methanol and mixtures thereof
and of a tertiary amine of formula $N(R^{24}R^{25}R^{26})$, wherein $R^{24}$, $R_{25}$ and $R^{26}$ are s independently selected among C1-C6 aliphatic group, preferably triethylamine; and
(iii) reacting the compound obtained in step (ii) with a basic compound selected among potassium carbonate, calcium carbonate and mixtures thereof.

Non limiting example of preferred complexes of formula (VI) is:

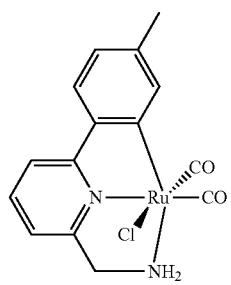

The pincer dicarbonyl complex 4 was synthesized from $[RuCl_2(CO)_2]_n$ and 6-(4-methylpheny)-2-(aminomethyl)pyridine in refluxing ethanol with triethylamine.

According to a further embodiment, the present disclosure may refer to complexes of formula (VII)

$$[M(CO)_2(CP)(NN)]W \quad (VII)$$

wherein M, (CP), (NN) and W are as defined in formula (1).
Preferably, R[23] may be —$CH_3$ and/or R[21]-R[22] may be a C6-C20 cycloaliphatic group or C6-C20 aromatic group, more preferably R[23] may be —$CH_3$ and/or R[21]-R[22] may be independently selected among phenyl and cyclohexyl group.

The present disclosure also refers to a process to obtain complexes of formula (VII) by:

(i) reacting a compound of formula $MX_2Y$, preferably of formula $MX_3$, more preferably of formula $MCl_3$, wherein M, X and Y are as defined above, with HCOOH, thereby obtaining an intermediate compound of formula $[MXY(CO)_2]_n$, preferably of formula $[MX_2(CO)_2]_n$, more preferably of formula $[MCl_2(CO)_2]_n$;

(ii) reacting the compound of formula $[MXY(CO)_2]_n$ with a (HCP) compound of formula (IVa)

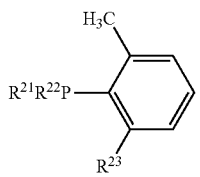

wherein $R^{21}$-$R^{23}$ are independently selected among H, C1-C20 aliphatic groups and C5-C20 aromatic groups, preferably $R^{23}$ may be —$CH_3$ and/or $R^{21}$-$R^{22}$ may be a C6-C20 cycloaliphatic group or C6-C20 aromatic group, more preferably $R^{23}$ may be —$CH_3$ and/or $R^{21}$-$R^{22}$ may be independently selected among phenyl and cyclohexyl group in the presence of a solvent, preferably selected among C1-C6 aliphatic alcohols, preferably selected among ethanol, methanol and mixtures thereof and of a tertiary amine of formula $N(R^{24}R^{25}R^{26})$, wherein $R^{24}$, $R^{25}$ and $R^{26}$ are independently selected among C1-C6 aliphatic group, preferably triethylamine; and (iii) reacting the compound obtained in step (ii) with a basic compound selected among potassium carbonate, calcium carbonate and mixtures thereof and a nitrogen-containing (NN) compound of formula Ia-Ic:

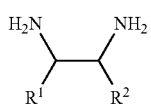 (Ia)

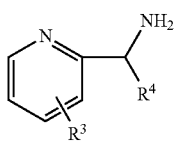 (Ib)

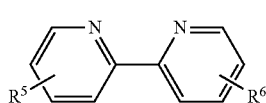 (Ic)

wherein $R^1$-$R^6$ are independently selected among H, C1-C20 aliphatic groups and C5-C20 aromatic groups, preferably $R^1$-$R^2$ may be independently selected among H and phenyl group and/or $R^3$-$R^6$ may be H.

Non limiting examples of preferred complexes of formula (VII) are:

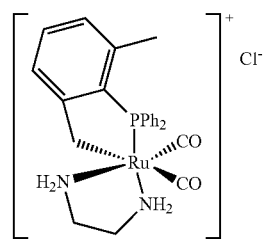 5

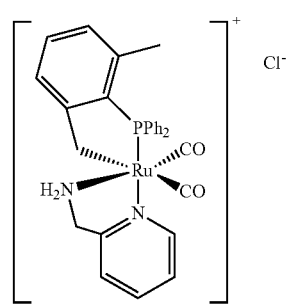 6

The cationic dicarbonyl cyclometallated complexes 5, 6 were prepared from $[RuCl_2(CO)_2]_n$ with (2,6-dimethylphenyl)diphenylphosphine in the presence of triethylamine and the bidentate nitrogen ligand ethylenediamine or 2-(aminomethyl)pyridine in ethanol.

According to a further embodiment, the present disclosure may refer to complexes comprising the ligand (IVa) to coordinate the metal, affording complexes of formula (VIII):

$MXY(CO)_2(HCP)_2$ (VIII)

wherein M, X, Y and HCP are as defined in formula (1), provided that when M is Ru and X=Y=Cl, $R^{23}$ is not hydrogen.

Preferably, $R^{23}$ may be —$CH_3$ and/or $R^{21}$-$R^{22}$ may be C6-C20 cycloaliphatic groups or C6-C20 aromatic group, more preferably $R^{23}$ may be —$CH_3$ and/or $R^{21}$-$R^{22}$ may be independently selected among phenyl and cyclohexyl group. The ortho-methyl group can be easily deprotonated, leading to the anionic bidentate ligand of the type (IVb) through the P and C atoms.

The present disclosure may also refer to a process to obtain complexes of formula (VIII) by:

(i) reacting a compound of formula $MX_2Y$, preferably of formula $MX_3$, more preferably of formula $MCl_3$, wherein M, X and Y are as defined above, with HCOOH, thereby obtaining an intermediate compound of formula $[MXY(CO)_2]_n$, preferably of formula $[MX_2(CO)_2]_n$, more preferably of formula $[MCl_2(CO)_2]_n$;

(ii) reacting the compound of formula $[MXY(CO)_2]_n$ with at least one (HCP) compound of formula (IVa)

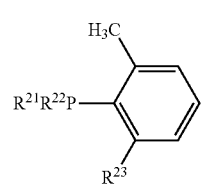 (IVa)

wherein
R$^{21}$-R$^{23}$ are independently selected among H, C1-C20 aliphatic groups and C5-C20 aromatic groups, preferably R$^{23}$ may be —CH$_3$ and/or R$^{21}$-R$^{22}$ may be a C6-C20 cycloaliphatic group or a C6-C20 aromatic group, more preferably R$^{23}$ may be —CH$_3$ and/or R$^{21}$-R$^{22}$ may be independently selected among phenyl and cyclohexyl group, in the presence of a solvent, preferably selected among C1-C6 aliphatic alcohols, more preferably among ethanol, methanol and mixtures thereof.

Non limiting examples of preferred complexes of formula (VIII) is:

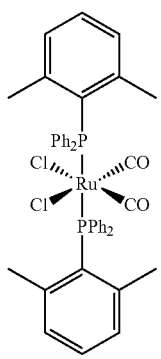

7

The dicarbonyl complex 7 was obtained by reaction of the polymer [RuCl$_2$(CO)$_2$]$_n$ with (2,6-dimethylphenyl)diphenylphosphine, in ethanol.

According to a further embodiment, the present disclosure may refer to a complex of formula (IX)

MX(CO)$_2$(CP)(HCP)     (IX)

wherein M, X, CP and HCP are as defined in formula (1), provided that when M is Ru and X is Cl, HCP is not 2,6-dimethylphenyl)diphenylphosphine (Hdmpp) and CP is not the anion of 2,6-dimethylphenyl)diphenylphosphine (dmpp).

Preferably, R$^{23}$ may be —CH$_3$ and/or R$^{21}$-R$^{22}$ may be a C6-C20 cycloaliphatic group or a C6-C20 aromatic group, more preferably R$^{23}$ may be —CH$_3$ and/or R$^{21}$-R$^{22}$ may be independently selected among phenyl group and cyclohexyl group.

The present disclosure may also refer to a process to obtain complexes of formula (IX) by:
(i) reacting a compound of formula MX$_2$Y, preferably of formula MX$_3$, more preferably of formula MCl$_3$, wherein M, X and Y are as defined above, with HCOOH, thereby obtaining an intermediate compound of formula [MXY(CO)$_2$]$_n$, preferably of formula [MX$_2$(CO)$_2$]$_n$, more preferably of formula [MCl$_2$(CO)$_2$]$_n$;
(ii) reacting the compound of formula [MXY(CO)$_2$]$_n$ with at least one (HCP) compound of formula (IVa)

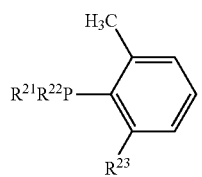

(IVa)

wherein
R$^{21}$-R$^{23}$ are independently selected among H, C1-C20 aliphatic groups and C5-C20 aromatic groups, preferably R$^{23}$ may be —CH$_3$ and/or R$^{21}$-R$^{22}$ may be a C6-C20 cycloaliphatic group or a C6-C20 aromatic group, more preferably R$^{23}$ may be —CH$_3$ and/or R$^{21}$-R$^{22}$ may be independently selected among phenyl and cyclohexyl group, in the presence of a solvent, preferably selected among C1-C6 aliphatic alcohols, more preferably among ethanol, methanol and mixtures thereof,
and of a tertiary amine of formula N(R$^{24}$R$^{25}$R$^{26}$), wherein R$^{24}$, R$^{25}$ and R$^{26}$ are independently selected among C1-C6 aliphatic group, preferably trimethylamine, thereby obtaining a pentacoordinate complex;
(iii) reacting the pentacoordinate complex with carbon monoxide in the presence of an organic solvent, preferably CH$_2$Cl$_2$.

The complex of formula (1) and of sub-formulas (V)-(IX) have been found to be highly active in transfer hydrogenation of ketones and aldehydes to alcohols and can be used in hydrogenation of the same compounds using molecular hydrogen.

A further aspect of the present disclosure is therefore the use of the complex of formula (1) or of sub-formulas (V)-(IX) as catalysts or pre-catalyst for the reduction reaction of ketones or aldehydes to alcohols by transfer hydrogenation or hydrogenation with molecular hydrogen.

In another aspect, the present disclosure refers to a process for the reduction of ketones or aldehydes to the corresponding alcohols comprising the following steps:
(a) mixing a catalyst or pre-catalyst with a solution comprising at least one base and at least one substrate selected among C3-C42 ketones and C2-C41 aldehydes thereby obtaining a mixture; and
(b) contacting said mixture with molecular hydrogen or with at least one hydrogen-donor, preferably selected among 2-propanol, sodium formate, ammonium formate, and a mixture of formic acid and triethylamine, said process being characterized in that the catalyst or pre-catalyst is a hexacoordinate complex of formula (1a):

[MX$_a$Y$_b$(CO)$_2$L$_c$L'$_d$]W$_e$     (1a)

wherein
M=Ru or Os;
X and Y are independently selected among halides, hydride, C1-C20 carboxylates and C1-C20 alkoxides;
W is selected among halides, C1-C20 carboxylates and C1-C20 alkoxides;
a, b, c and e are independently 0 or 1, d is 0, 1 or 2;
L is a nitrogen-containing ligand selected among:
(I) a (NN) compound of formula Ia-Ic:

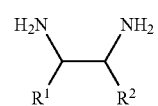

(Ia)

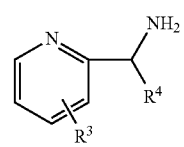

(Ib)

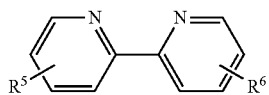
(Ic)

(II) a (HCNN) compound of formula IIa-IIb:

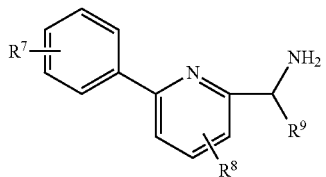
(IIa)

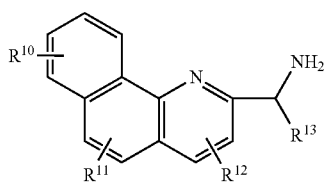
(IIb)

(III) a (CNN) ligand of formula IIc-IId:

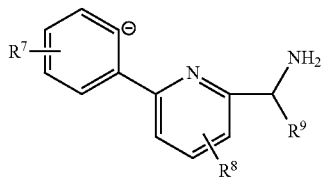
(IIc)

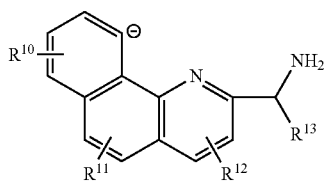
(IId)

wherein $R^1$-$R^{13}$ are independently selected among H, C1-C20 aliphatic groups and C5-C20 aromatic groups, preferably $R^1$ and $R^2$ may be independently selected among H and a phenyl group and/or $R^3$-$R^6$ and $R^8$-$R^{13}$ may be H and/or $R^7$ may be 4-methyl; and L' is at least one phosphorus-containing ligand selected among a HCP compound of formula (IVa) and a CP ligand of formula (IVb)

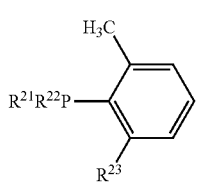
(IVa)

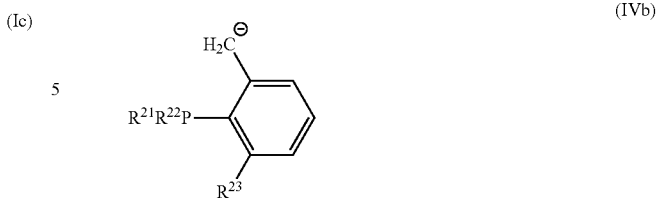
(IVb)

wherein $R^{21}$-$R^{23}$ are independently selected among H, C1-C20 aliphatic groups and C5-C20 aromatic groups, preferably $R^{23}$ may be —CH$_3$ and/or $R^{21}$-$R^{22}$ may be a C6-C20 cycloaliphatic group or a C6-C20 aromatic group, more preferably $R^{23}$ may be —CH$_3$ and/or $R^{21}$-$R^{22}$ may be independently selected among phenyl and cyclohexyl group; provided that when M is Ru and a=1; b=c=e=0; d=2 and X=Cl, HCP is not 2,6-dimethylphenyl)diphenylphosphine (Hdmpp) and CP is not the anion of 2,6-dimethylphenyl)diphenylphosphine (dmpp).

The complex of formula (1) and sub-formulas (VIII) and (IX) containing only phosphorus-containing ligands L' may be conveniently used as pre-catalyst in a (transfer)hydrogenation process carried out in the presence of a nitrogen-containing ligand L.

Therefore, according to an embodiment, the present disclosure may refer to a process for the reduction of ketones or aldehydes to the corresponding alcohols, comprising:

(a) mixing a pre-catalyst complex of formula (2) with a solution comprising
at least one base and at least one substrate selected among C3-C42 ketones and C2-C41 aldehydes; and
at least one nitrogen-containing compound L selected among:
(I) a NN compound of formula Ia to Ic:

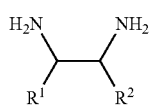
(Ia)

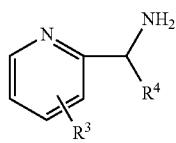
(Ib)

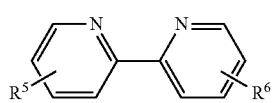
(Ic)

(II) a HCNN compound of formula IIa-IIb:

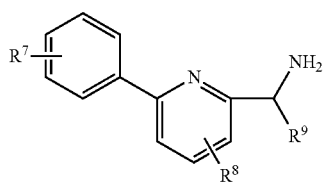
(IIa)

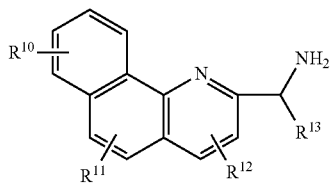

(IIb)

wherein $R^1$-$R^{13}$ are independently selected among H, C1-C20 aliphatic groups and C5-C20 aromatic groups, preferably $R^1$ and $R^2$ may be independently selected among H and a phenyl group and/or $R^3$-$R^6$ and $R^8$-$R^{13}$ may be H and/or $R^7$ may be 4-methyl, thereby obtaining a mixture and (b) contacting said mixture with molecular hydrogen or with at least one hydrogen-donor, preferably selected among 2-propanol, sodium formate, ammonium formate and a mixture of formic acid and triethylamine, wherein said pre-catalyst has formula (2):

wherein

M=Ru or Os;

X and Y are independently selected among halides, hydride, C1-C20 carboxylates and C1-C20 alkoxides;

a and b are independently 0 or 1, d is 1 or 2;

L' is at least one phosphorus-containing ligand selected among a HCP compound of formula (IVa) and a CP ligand of formula (IVb)

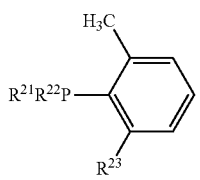

(IVa)

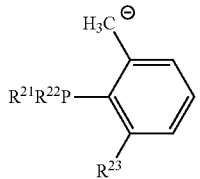

(IVb)

wherein $R^{21}$-$R^{23}$ are independently selected among H, C1-C20 aliphatic groups and C5-C20 aromatic groups, preferably $R^{23}$ may be —CH$_3$ and/or $R^{21}$-$R^{22}$ may be a C6-C20 cycloaliphatic group or a C6-C20 aromatic group, more preferably $R^{23}$ may be —CH$_3$ and/or $R^{21}$-$R^{22}$ may be independently selected among phenyl and cyclohexyl group; provided that when M is Ru and a=1; b=0; d=2 and X=Cl, HCP is not 2,6-dimethylphenyl)diphenylphosphine (Hdmpp) and CP is not the anion of 2,6-dimethylphenyl)diphenylphosphine (dmpp).

Preferably, the nitrogen-containing compound may be selected among NN compounds of formula (Ia) to (Ic)

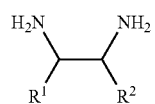

(Ia)

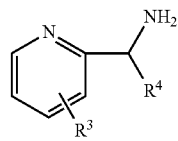

(Ib)

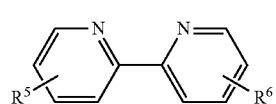

(Ic)

wherein $R^1$-$R^6$ are independently selected among H, C1-C20 aliphatic groups and C5-C20 aromatic groups. More preferably, the nitrogen-containing compound may be selected among ethylenediamine and 2-(aminomethyl)pyridine.

In a further embodiment, the present disclosure may refer to a process for the reduction of ketones or aldehydes to the corresponding alcohols as described above, wherein the catalyst or pre-catalyst is a complex of formula (1a) or (2) provided that when M is Ru and a=b=1, c=e=0, d=2 and X=Y=Cl, $R^{23}$ is not hydrogen.

In a further embodiment, the present disclosure may refer to a process for the reduction of ketones or aldehydes to the corresponding alcohols as described above, wherein the catalyst or pre-catalyst is a complex of formula (1a), provided that when M is Ru and a=b=c=1; d=e=0 and X=Y=Cl, L is not ethylenediamine, 2-(aminomethyl)pyridine or bipyridine, preferably L is not a (NN) ligand.

The complex of formula (1), (V) and (VI) containing only nitrogen-containing ligands L may be conveniently used as pre-catalyst in a (transfer)hydrogenation process carried out in the presence of a phosphorus-containing ligand L'.

Therefore, according to an embodiment, the present disclosure refers to a process for the reduction of ketones or aldehydes to the corresponding alcohols, comprising:

(a) mixing a pre-catalyst complex of formula (3) with a solution comprising at least one base and at least one substrate selected from the group consisting of C3-C42 ketones and C2-C41 aldehydes at least one phosphorus-containing compound selected among:

(I) a phosphine (P) selected among:

a phosphine of formula PR$^{16}$R$^{17}$R$^{18}$, wherein $R^{16}$-$R^{18}$ are independently selected among H, C1-C20 aliphatic groups and C5-C20 aromatic groups;

an optically active phosphine selected among (S)-neomenthyldiphenylphosphine and (R)-(+)-2-(diphenylphosphino)-2'-methoxy-1,1'-binaphthyl;

(i) a diphosphine (PP) selected among:

a diphosphine of formula P(R$^{19}$)$_2$—Z—P(R$^{20}$)$_2$, wherein Z is a C2-C4 hydrocarbon chain or ferrocene optionally substituted with C1-C20 aliphatic groups, and wherein $R^{19}$ and $R^{20}$ are independently selected among C1-C20 aliphatic groups and C5-C20 aromatic groups;

an optically active diphosphine selected from the group consisting of (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2-[bis(3,5-dimethyl-4-methoxyphenyl)phosphine]ferrocenyl}ethyldicyclohexyl phosphine and (2R,4R)-2,4-bis(diphenylphosphine)pentane, thereby obtaining a mixture; and (b) contacting said mixture with molecular hydrogen or with at least one hydrogen-donor, preferably selected among 2-propanol, sodium formate, ammonium formate and a mixture of formic acid and triethylamine, wherein said pre-catalyst has formula (3)

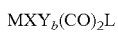  (3)

wherein

M=Ru or Os;

X and Y are independently selected among halides, hydride, C1-C20 carboxylates and C1-C20 alkoxides;

b is 0 or 1

L is a nitrogen-containing ligand selected among:

(I) a (NN) compound of formula Ia-Ic:

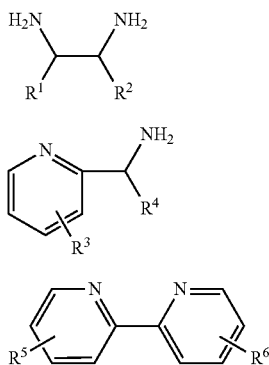

(II) a (HCNN) compound of formula IIa-IIb:

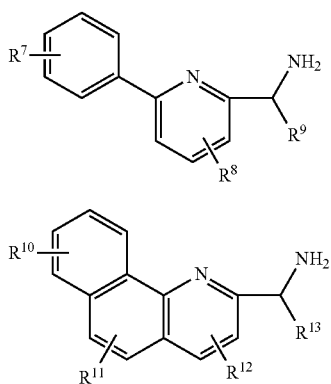

(III) a (CNN) ligand of formula IIc-IId:

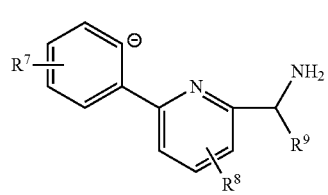

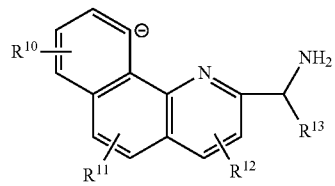

wherein $R^1$-$R^{13}$ are independently selected among H, C1-C20 aliphatic groups and C5-C20 aromatic groups preferably $R^1$ and $R^2$ may be independently selected among H and a phenyl group and/or $R^3$-$R^6$ and $R^8$-$R^{13}$ may be H and/or $R^7$ may be 4-methyl.

In a further embodiment, the present disclosure may refer to a process for the reduction of ketones or aldehydes to the corresponding alcohols as described above, wherein the pre-catalyst is a complex of formula (3), with the further proviso that when M is Ru, b=1 and X=Y=Cl, L is not ethylenediamine, 2-(aminomethyl)pyridine or bipyridine, preferably L is not a (NN) ligand.

In a further embodiment, the present disclosure may refer to complexes of formula (1), (1a), (2), (3) and of sub-formulas (V)-(IX) as described above in which M is Ru. In a further embodiment, the present disclosure may refer to a complex of formula (1), (1a), (2), (3) and sub-formulas (V), (VI), (VIII) and (IX) as described above, wherein X and/or Y is chlorine, preferably X and Y are chlorine.

In a further embodiment, the present disclosure may refer to a complex of formula (1) and (1a) and sub-formula (VII) as described above, wherein W is chlorine.

The complex of formula (1) and sub-formula (VII) containing both nitrogen- and phosphorus-containing ligands may be conveniently used as catalyst in transfer hydrogenation or hydrogenation with molecular hydrogen.

In the catalytic reduction processes described above, the step (a) of the reduction reaction is conducted in the presence of a base, wherein said base may be an alkali metal alkoxide preferably selected among sodium iso-propoxide, potassium tert-butoxide, potassium hydroxide, potassium carbonate, more preferably is potassium tert-butoxide.

In a preferred embodiment, the present disclosure may refer to a process for the reduction of ketones or aldehydes to the corresponding alcohols, wherein step (b) is carried out by contacting said mixture with molecular hydrogen.

According to a further embodiment, in the process of the disclosure in step (a) the base is sodium iso-propoxide and in step (b) the mixture is contacted with at least one hydrogen donor.

The transfer hydrogenation reduction process of the present disclosure may be carried out at a temperature of 30-82° C.

In one embodiment, the reduction reactions by hydrogenation with $H_2$ may be carried out at 40-70° C. under hydrogen atmosphere (5-30 atm) in presence of methanol or ethanol as solvent. Under these reaction conditions the conversion of the ketone or aldehyde to alcohol is in the range from good to complete.

The complex of the present disclosure may be used for the preparation of alcohols, also chiral, by the reduction of C3-C41 ketones and of C2-C41 aldehydes.

In the process of the disclosure, at least one substrate may be selected among:
- at least one C3-C41 ketone selected among compounds of formula $R^{27}C(=O)R^{28}$ wherein $R^{27}$ and $R^{28}$ are independently selected among C1-C20 aliphatic, substituted aliphatic and aromatic groups, wherein optionally $R^{27}$ and $R^{28}$ are linked to form a cycle;
- at least one C2-C41 aldehyde is selected among compounds of formula $R^{29}C(=O)H$, wherein $R^{29}$ is selected among C1-C40 aliphatic, substituted aliphatic and aromatic groups; and
- mixtures thereof.

According to an embodiment, in the process of the present disclosure the molar ratio substrate/catalyst or pre-catalyst may range from 1000/1 to 100000/1, preferably from 1000/1 to 50000/1.

According to an embodiment, in the process of the present disclosure the molar ratio ligand/catalyst or pre-catalyst may range from 1/1 to 5/1, preferably from 1/1 to 2/1. According to a further embodiment, in the process of the present disclosure the molar ratio substrate/base may range from 20 to 50.

These and other objects as well as features and advantages of the present invention will be better understood from the following detailed description and from the preferred embodiments which are given for illustrative purposes and not limitative of the invention itself.

All the syntheses of the complexes and transfer hydrogenation reactions were carried out under inert gas atmosphere and the solvents used were dried and distilled before use. All the procedures of hydrogenation were carried using technical grade solvents.

Example 1: Synthesis of the Complex $RuCl_2(CO)_2(Hamtp)$ (1)

The complex $RuCl_3 \cdot xH_2O$ (83.2 mg, 0.40 mmol, 1 equiv) was added to 6 mL of HCOOH and the suspension was stirred in a sealed tube at 110° C. for 2 h (until the mixture turned yellow and homogenous), obtaining $[RuCl_2(CO)_2]_n$. The solvent was evaporated under reduced pressure and the residue was dissolved in 6 mL of distilled EtOH. After addition of the ligand Hamtp (78.1 mg, 0.39 mmol, 1 equiv) the solution was stirred at 80° C. overnight. The solution was evaporated under reduced pressure and the residue was dissolved in 2 mL of $CHCl_3$. The solution was stirred for 1 h at room temperature and the complex was precipitated by addition of 10 mL ethyl ether. After filtration the solid was washed 2 times with 5 mL of ethyl ether, one time with 5 mL of n-pentane and dried under reduced pressure. Yield: 105.3 mg (80%). Anal. Calcd (%) for $C_{15}H_{14}Cl_2N_2O_2Ru$: C, 42.27; H, 3.31; N, 6.57, Found: C, 42.10; H, 3.26; N, 6.59. $^1H$ NMR (200 MHz, $CDCl_3$) δ 7.80-7.30 (m, 7H, aromatic hydrogens), 4.77 (br, 2H, $NH_2$), 4.19 (br, 2H, $NCH_2$), 2.43 (s, 3H, $CH_3$); $^{13}C$ NMR (50 MHz, $CDCl_3$) δ 195.5, 190.3, 164.8-120.2 (m, aromatic carbons), 51.2, 21.5. IR (cm$^{-1}$): 2067, 1998.

Example 2: Synthesis of the Complex $RuCl_2(CO)_2(Hambq)$ (2)

The complex $[RuCl_2(CO)_2]_n$ (203 mg, 0.89 mmol, 1 equiv) suspended in ethanol (10 mL), was reacted with the ligand Hambq (202 mg, 0.97 mmol, 1.1 equiv). The suspension was stirred at 80° C. overnight and the solvent was evaporated under reduced pressure. The residue was dissolved in $CH_2Cl_2$ (4 mL) and the solution was stirred at room temperature for 4 h. The volume was reduced to about 1 mL. The complex was precipitated by addition of 10 mL of ethyl ether. The obtained solid was filtered, washed two times with 5 mL of ethyl ether, one time with 5 mL of n-pentane and dried under reduced pressure. Yield: 190 mg (49%). Anal. Calcd (%) for $C_{16}H_{12}Cl_2N_2O_2Ru$:C, 44.05; H, 2.77; N, 6.42; found: C, 44.10; H, 2.78; N, 6.38. $^1H$ NMR (200 MHz, $CD_2Cl_2$) δ 8.25 (d, J=8.3 Hz, 1H), 8.11-7.41 (m, 7H), 4.97-4.79 (m, 1H), 4.77-4.60 (m, 1H), 4.59-4.45 (m, 1H), 3.82-3.56 (m, 1H).; $^{13}C$ NMR (50 MHz, $CD_2Cl_2$) δ 199.9, 190.3, 159.9, 150.5, 141.7, 137.4, 136.7, 134.1, 129.6, 129.3, 127.7, 125.1, 122.3, 121.7, 117.2, 65.5.

Example 3: Synthesis of the Complex $RuCl_2(CO)_2(Hambq^{pH})$ (3)

The complex $[RuCl_2(CO)_2]_n$ (227 mg, 1.00 mmol, 1 equiv) suspended in ethanol (10 mL), was reacted with the ligand Hambq (332 mg, 1.17 mmol, 1.2 equiv). The suspension, was stirred at 80° C. overnight and the solvent was evaporated under reduced pressure. The residue was dissolved in $CH_2Cl_2$ (4 mL) and the solution was stirred at room temperature for 4 h. The volume was reduced to about 1 mL. The complex was precipitated by addition of 10 mL of ethyl ether. The obtained solid was filtered, washed two times with 5 mL of ethyl ether, once with 5 mL of n-pentane and dried under reduced pressure. Yield: 370 mg (72%). Anal. Calcd (%) for $C_{22}H_{16}Cl_2N_2O_2Ru$: C, 51.57; H, 3.15; N, 5.47, found: C, 51.45; H, 3.32; N, 5.71. $^1H$ NMR (200 MHz, $CD_3OD$) δ 9.60-9.41 (m, 1H), 8.06-7.40 (m, 11H), 4.62 (s, 2H). $^{13}C$ NMR (50 MHz, $CD_2Cl_2$) δ 201.2, 194.5, 161.7, 158.4, 157.2, 150.5, 142.6, 137.8, 137.4, 134.6, 130.1, 129.9, 129.7, 129.4, 129.2, 124.0, 122.0, 121.3, 118.1, 46.1.

Example 4: Synthesis of the Complex $RuCl(Amtp)(CO)_2$ (4)

The compound $RuCl_3 \cdot xH_2O$ (107.3 mg, 0.51 mmol, 1 equiv) was suspended in 7 mL of HCOOH and the mixture was stirring at 110° C. for 2 h. The solvent was evaporated under reduced pressure and the residue, dissolved in 7 mL of n-BuOH, was reacted with the ligand Hampt (100.8 mg, 0.51 mmol, 1 equiv) and the base $Et_3N$ (1.4 mL, 10.3 mmol, 20 equiv). The mixture was stirred at 110° C. overnight, the solvent was evaporated under reduced pressure. The residue was dissolved in 2 mL of $CHCl_3$ and the base $K_2CO_3$ (320 mg, 2.32 mmol, 4.5 equiv) was added. After stirring for 2 h at room temperature, the mixture was filtrated. The filtrate was concentrated to about 1 mL and the complex was precipitated by addition of 10 mL of ethyl ether. The obtained solid was filtered, washed two times with 3 mL of ethyl ether, one time 3 mL of with n-pentane and dried at reduced pressure. Yield 61.2 mg (%). Anal. Calcd (%) for $C_{15}H_{13}ClN_2O_2Ru$: C, 46.22; H, 3.36; N, 7.19. Found:C, 46.25; H, 3.30; N, 7.01. $^1H$ NMR (200 MHz, $CDCl_3$) δ 7.82-7.61 (m, 2H), 7.63-7.45 (m, 2H), 7.07 (d, J=6.9 Hz, 1H), 6.85 (d, J=7.5 Hz, 1H), 4.61 (dd, J=16.6, 6.7 Hz, 1H), 4.39 (dd, J=17.6, 8.1 Hz, 1H), 4.20-4.02 (m, 1H), 3.51-3.28 (m, 1H), 2.30 (s, 3H). $^{13}C$ NMR (50 MHz, $CDCl_3$) δ 200.4 (s, CO), 193.7 (s, CO), 163.5 (s, NCC), 162.8 (s, NCC), 157.3 (s, Cq aro), 156.27 (s, Cq aro), 142.2 (s, Cq aro), 140.8 (s, C—H aro), 138.7 (s, C—H aro), 125.0 (C—H aro), 124.4

(s, C—H aro), 117.5 (s, C—H aro), 117.0 (s, C—H aro), 60.4 (s, $CH_2$), 21.6 (s, $CH_3$). IR ($cm^{-1}$): 2028, 1958.

Example 5: Synthesis of the Complex [Ru{(2-$CH_2$-6-Me-$C_6H_3$)$PPh_2$)(CO)$_2$(en)]Cl (5)

The compound $RuCl_3 \cdot xH_2O$ (207.9 mg, 1 mmol, 1 equiv) was suspended in 5 mL of HCOOH and the mixture was stirred in a sealed tube at 100° C. for 2 h (until the mixture became yellow and homogenous), obtaining [$RuCl_2(CO)_2]_n$. The solvent was evaporated under reduced pressure and the residue was dissolved in 6 mL of distilled EtOH. The solution was reacted with the ligand (2,6-$Me_2C_6H_3$)$PPh_2$ (881.9 mg, 3 mmol, 3 equiv) and $Et_3N$ (680 μL, 5 mmol, 5 equiv). After stirring at 80° C. overnight, the volume was reduced to about half and fitered. The solid was washed 3 times with 3 mL of EtOH, 2 times with 3 mL of ethyl ether, on time with 2 mL of n-pentane and dried under reduced pressure, affording the complex [RuCl{(2-$CH_2$-6-Me-$C_6H_3$)$PPh_2$}(CO)$_2$[(2,6-$Me_2C_6H_3$)$PPh_2$]. Said complex [RuCl{(2-$CH_2$-6-Me-$C_6H_3$)$PPh_2$}(CO)$_2$[(2,6-$Me_2C_6H_3$)$PPh_2$] (252 mg, 0.33 mmol, 1 equiv), suspended in 5 ml of methanol, was reacted with the ligand en (45 μL, 0.67 mmol, 2.1 equiv) and $CaCO_3$ (16 mg, 0.16 mmol, 0.5 equiv). After stirring at 65° C. overnight, the mixture was filtered. The volume of the filtrate was reduced to about half, and the complex precipitated by adding 7 mL of n-pentane. The obtained solid was filtered and washed two times with 2 mL of ethyl ether and dried under reduced pressure. Yield 156 mg (88%). Anal. Calcd (%) for $C_{24}H_{26}ClN_2O_2PRu$: C, 53.19; H, 4.84; N, 5.17, Found: C, 53.32; H, 4.79; N, 5.02. $^1$H NMR (200 MHz, $CD_3OD$) δ 7.61-7.26 (m, 12H), 6.99 (dd, J=6.6, 3.2 Hz, 1H), 4.35-4.14 (m, 1H), 4.12-3.84 (m, 1H), 2.93 (d, J=15.0 Hz, 1H), 2.51 (d, J=14.9 Hz, 1H), 1.64 (s, 3H). $^{13}$C NMR (50 MHz, $CD_3OD$) δ 201.3 (d, J=13.5 Hz), 191.9 (d, J=6.5 Hz), 163.3 (d, J=33.1 Hz), 142.0 (d, J=1.7 Hz), 136.3, 135.22, 133.4 (d, J=10.2 Hz), 133.0 (d, J=2.7 Hz), 132.1 (d, J=2.5 Hz), 131.9, 131.6 (d, J=2.4 Hz), 131.5 (d, J=10.5 Hz), 130.7 (d, J=10.0 Hz), 130.2 (d, J=10.5 Hz), 129.9, 129.6, 129.2 (d, J=6.5 Hz), 45.4 (d, J=3.9 Hz), 31.9 (d, J=4.1 Hz), 22.3 (d, J=3.9 Hz). $^{31}$P NMR (81 MHz, $CD_3OD$) δ 64.6.

Example 6: Synthesis of the Complex [Ru{(2-$CH_2$-6-Me-$C_6H_3$)$PPh_2$)(CO)$_2$(ampy)]Cl (6)

The complex [RuCl{(2-$CH_2$-6-Me-$C_6H_3$)$PPh_2$}(CO)$_2$[(2,6-$Me_2C_6H_3$)$PPh_2$] (251 mg, 0.32 mmol, 1 equiv) prepared as in Example 5, suspended in 5 ml of methanol, was reacted with ampy (68 μL, 0.66 mmol, 2.1 equiv) and $CaCO_3$ (16 mg, 0.16 mmol, 0.5 equiv). After stirring at 65° C. overnight, the solution was filtered. The volume of the filtrate was reduced by about half, and the complex was precipitated by adding 7 mL of n-pentane.

The obtained solid was filtered and washed two times with 2 mL of ethyl ether and dried under reduced pressure. Yield 83 mg (44%). Anal. Calcd (%) for $C_{28}H_{26}ClN_2O_2PRu$: C, 57.00; H, 4.44; N, 4.75, Found: C, 57.32; H, 4.24; N, 4.53. $^1$H NMR (200 MHz, $CD_3OD$) δ 8.74 (d, J=5.5 Hz, 1H), 7.96 (t, J=7.3 Hz, 1H), 7.71-7.28 (m, 14H), 7.14-6.99 (m, 1H), 4.26-4.10 (m, 2H), 2.92 (d, J=15.4 Hz, 1H), 2.66 (d, J=15.4 Hz, 1H), 1.70 (s, 3H). $^{13}$C NMR (50 MHz, $CD_3OD$) δ 201.3 (d, J=14.6 Hz), 191.5 (d, J=6.5 Hz), 162.8, 162.6 (d, J=32.1 Hz), 153.7, 143.1 (d, J=2.2 Hz), 140.3, 135.1, 133.2, 133.2 (d, J=10.3 Hz), 132.4 (d, J=2.5 Hz), 132.0 (d, J=2.7 Hz), 131.8 (d, J=10.4 Hz), 131.5, 130.9 (d, J=10.2 Hz), 130.4 (d, J=10.7 Hz), 129.6 (d, J=6.4 Hz), 129.5 (d, J=3.7 Hz), 126.3 (d, J=2.0 Hz), 123.3 (d, J=1.9 Hz), 52.2 (d, J=3.4 Hz), 33.9 (d, J=3.9 Hz), 22.3 (d, J=3.9 Hz). $^{31}$P NMR (81 MHz, $CD_3OD$) δ 64.4. IR ($cm^{-1}$): 2020, 1957.

Example 7: Synthesis of the Complex $RuCl_2(CO)_2$[(2,6-$Me_2C_6H_3$)$PPh_2]_2$ (7)

The complex [$RuCl_2(CO)_3]_2$ (50 mg, 0.1 mmol, 1 equiv) suspended in 5 mL of distilled EtOH, was reacted with the ligand (2,6-$Me_2C_6H_3$)$PPh_2$ (126 mg, 0.44 mmol, 4.4 equiv). After stirring at 80° C. overnight, the solvent was evaporated under reduced pressure and the residue was dissolved in 2 mL of $CHCl_3$ and stirred at room temperature for further 2 h. The volume was reduced to about half and the complex was precipitated by addition of 5 mL of ethyl ether. The obtained solid was filtrated, washed 2 times with 3 mL of ethyl ether, once with 3 mL of n-pentane and dried under reduced pressure. Yield 133 mg (84%). Anal. Calcd (%) for $C_{42}H_{38}Cl_2O_2P_2Ru$: C, 62.38; H, 4.74, Found: C, 62.60; H, 4.98. $^1$H NMR (200 MHz, $CD_2Cl_2$) δ 738-7.18 (m, 26H), 2.12 (s, 12H). $^{13}$C NMR (50 MHz, $CD_2Cl_2$) δ. $^{31}$P NMR (81 MHz, $CD_2Cl_2$) δ 10.1. IR ($cm^{-1}$): 2039, 2001.

Example 8: Catalytic Reduction by Transfer Hydrogenation of Ketones and Aldehydes with Complexes of Examples 1-6

The catalyst solution was prepared in a 10 mL Schlenk by adding 5 mL of 2-propanol to the chosen ruthenium complex (0.02 mmol). By stirring, the complex dissolved over a period of a few minutes. Separately, in a second Schlenk (20 mL), 250 μL of the previously prepared solution containing the catalyst and 200 μL of a 0.1 M sodium iso-propoxide solution in 2-propanol were added subsequently to the ketone or aldehyde solution (1 mmol) in 10 mL of 2-propanol under reflux.

The start of the reaction was considered to be when the base was added. The molar ratio of substrate/catalyst (S/C) varied from 1000/1 to 100000/1. The molar ratio substrate/base was in the range of 10/1 to 100/1. The reaction was performed in the range of 20 to 82° C. (boiling point of 2-propanol).

For the reactions, in which the catalyst was formed in situ, a pre-catalyst solution was prepared by adding 5 mL of 2-propanol to the pre-catalyst (0.02 mmol) and the corresponding ligand (0.1 mmol) (see Tables 2 and 3) and the solution was stirred for 30 min at reflux. The solution of the in situ formed catalyst was used in the reduction reaction as described above.

The results of the GC analysis for the reduction of acetophenone are reported in Table 2, while those for other ketones and aldehydes are shown in Table 3.

TABLE 2

Catalytic transfer hydrogenation of acetophenone (0.1M) to 1-phenylethanol with the complexes 1-6 in the presence of a ligand with NaOiPr 2 mol %

| Complex | S/C | Ligand | L/C | Conversion % (min) | TOF ($h^{-1}$) |
|---|---|---|---|---|---|
| 1 | 1000 | $PPh_3$ | 2 | 100 (60) | 1000 |
| 1 | 1000 | $PCy_3$ | 2 | 100 (1) | >30000 |
| 1 | 50000 | $PCy_3$ | 2 | 100 (15) | 100000 |
| 2 | 1000 | $PPh_3$ | | 97 (60) | |
| 2 | 1000 | $PCy_3$ | | 96 (15) | |
| 3 | 1000 | $PPh_3$ | | 97 (60) | |
| 3 | 1000 | $PCy_3$ | | 96 (15) | |

TABLE 2-continued

Catalytic transfer hydrogenation of acetophenone
(0.1M) to 1-phenylethanol with the complexes 1-6 in the
presence of a ligand with NaOiPr 2 mol %

| Complex | S/C | Ligand | L/C | Conversion % (min) | TOF ($h^{-1}$) |
|---|---|---|---|---|---|
| 5 | 1000 | — | | 13 (1) | |
| 6 | 1000 | — | | 100 (0, 17) | 3000 |

TABLE 3

Catalytic transfer hydrogenation of ketones and aldehydes
(0.1M) to alcohols with the complexes 1-3 in the
presence of a ligand with NaOiPr 2 mol %

| Complex | Substrate | S/C | Ligand | Conversion % (min) | TOF ($h^{-1}$) |
|---|---|---|---|---|---|
| 1 | isobutyrophenone | 10000 | $PCy_3$ | 100 (60) | 1000 |
| 1 | pivalophenone | 10000 | $PCy_3$ | 100 (1) | >30000 |
| 1 | benzophenone | 10000 | $PCy_3$ | 100 (15) | 100000 |
| 1 | camphor | 2000 | $PCy_3$ | 97 (60) | |
| 1 | pivalone | 10000 | $PCy_3$ | 96 (15) | |
| 1 | cyclohexanone | 10000 | $PCy_3$ | 97 (60) | |
| 1 | allylacetone | 10000 | $PCy_3$ | 96 (15) | |
| 2 | benzaldehyde | 1000 | $PPh_3$ | 100 (2) | 12000 |
| 2 | benzaldehyde | 1000 | $PCy_3$ | 100 (36) | 8000 |
| 3 | benzaldehyde | 1000 | $PPh_3$ | 100 (60) | 1000 |
| 3 | benzaldehyde | 1000 | $PCy_3$ | 100 (1) | >30000 |

The experimental results show that with the complex 1 in the presence of $PCy_3$, the reduction of linear, cyclic and aryl alkyl ketones, and aldehydes to the corresponding alcohols in 2-propanol under reflux was extremely fast and was complete within a few minutes, using a substrate/catalyst ratios equal to 50000 in the case of reduction of acetophenone.

The turnover frequency values (TOF) were up to 100000 $h^{-1}$, depending on the steric and electronic characteristics of the substrate (Tables 2 and 3).

Example 9: Catalytic Reduction of Ketones with Complexes of Examples 1-7 Using Molecular Hydrogen The hydrogenation reactions were performed in an 8 vessels Endeavor Parr apparatus. The vessels were charge with the catalysts (2.5 μmol). The vessels were closed, charged with 5 bar of $N_2$ and slowly vented five times. The ketone (0.6 mL, 5 mmol), optionally ligand (5 μmol), the solvent (0.9 mL of methanol or ethanol) and 1 mL of a solution of t-BuOK 0.1 M were added. The vessels were charged with 20 bar of $H_2$ and slowly vented four times. The vessel was charged to 30 bars and heated to 70° C. The molar ratio of substrate/catalyst varied from 2000/1 to 25000/1. The molar ratio of substrate/base were 10/1 to 100/1. The hydrogen uptake was calculated by the apparatus and the results of the GC analysis at the end of the runs are shown in Tables 4 for the catalytic reduction of acetophenone and in Table 5 for other substrates.

TABLE 4

Catalytic hydrogenation of acetophenone to 1-phenylethanol in the
presence of the complexes 1-3, 5-7 in the presence of a ligand

| Complex | S/C | Ligand | Solvent | Base (%) | Conversion % (h) | TOF ($h^{-1}$) |
|---|---|---|---|---|---|---|
| 1 | 2000 | $PPh_3$ | EtOH | t-BuOK (2) | 34 (16) | |
| 1 | 2000 | $PCy_3$ | EtOH | t-BuOK (2) | 46 (16) | |
| 1 | 2000 | $PCy_3$ | MeOH | t-BuOK (5) | 100 (16) | |
| 2 | 2000 | $PCy_3$ | MeOH | t-BuOK (5) | 100 (16) | |
| 3 | 2000 | $PCy_3$ | MeOH | t-BuOK (5) | 100 (16) | |
| 5 | 2000 | — | EtOH | t-BuOK (2) | 100 (16) | |
| 5 | 10000 | — | EtOH | t-BuOK (2) | 44 (16) | |
| 5 | 2000 | — | MeOH | t-BuOK (2) | 100 (16) | |
| 5 | 10000 | — | MeOH | t-BuOK (2) | 95 (3) | 4450[a] |
| 5 | 25000 | — | MeOH | t-BuOK (2) | 97 (22) | 3300[a] |
| 6 | 2000 | — | EtOH | t-BuOK (2) | 100 (16) | |
| 6 | 10000 | — | EtOH | t-BuOK (2) | 11 (16) | |
| 6 | 2000 | — | MeOH | t-BuOK (2) | 100 (16) | |
| 6 | 10000 | — | MeOH | t-BuOK (2) | 99 (2) | 13500[a] |
| 6 | 25000 | — | MeOH | t-BuOK (2) | 97 (22) | 4000[a] |
| 7 | 2000 | en | EtOH | t-BuOK (2) | 100 (16) | |
| 7 | 2000 | ampy | EtOH | t-BuOK (2) | 100 (16) | |

[a] Reactions performed in 50 mL high pressure vessel (Parr autoclave)

TABLE 5

Catalytic hydrogenation of ketones to alcohols in the presence
of the complexes 5 and 6 in ethanol with t-BuOK 2 mol %

| Complex | Ketone | S/C | Conversion % (h) |
|---|---|---|---|
| 5 | 2-octanone | 1000 | 100 (3) |
| 5 | isobutyrophenone | 1000 | 33 (3) |
| 5 | tetralone | 10000 | 1 (16) |
| 5 | 2'-Me-acetophenone | 10000 | 100 (16) |
| 5 | 4'-MeO-acetophenone | 500 | 100 (3) |
| 5 | 4'-NO2-acetophenone | 10000 | 2 (16) |
| 5 | benzophenone | 500 | 100 (3) |
| 5 | benzoin | 10000 | 9 (16) |
| 5 | 2'-Cl-acetophenone | 10000 | 100 (16) |
| 6 | 2-octanone | 1000 | 100 (3) |
| 6 | isobutyrophenone | 1000 | 100 (3) |
| 6 | tetralone | 10000 | 1 (16) |
| 6 | 2'-Me-acetophenone | 10000 | 100 (16) |
| 6 | 4'-MeO-acetophenone | 500 | 100 (3) |
| 6 | 4'-NO2-acetophenone | 10000 | 1 (16) |
| 6 | benzophenone | 500 | 99 (3) |
| 6 | benzoin | 10000 | 6 (16) |
| 6 | 2'-Cl-acetophenone | 10000 | 100 (16) |

The invention claimed is:
1. A hexacoordinate complex of Formula (V), (VI, (VII), (VIII), or (IX):

$$MXY(CO)_2(HCNN) \quad (V)$$

$$MX(CO)_2(CNN) \quad (VI)$$

[M(CO)₂(CP)(NN)]W  (VII)

MXY(CO)₂(HCP)₂  (VIII)

MX(CO)₂(CP)(HCP)  (IX)

wherein:

M is Ru or Os;

X and Y are, each independently, halide, hydride, C1-C20 carboxylate, or C1-C20 alkoxide, W is halide, C1-C20 carboxylate, or C1-C20 alkoxide;

(I) (NN) is a compound of formula Ia, Ib or Ic:

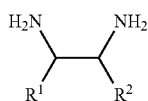
(Ia)

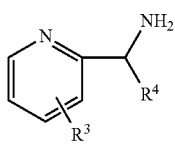
(Ib)

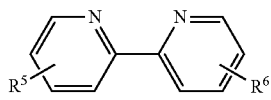
(Ic)

(II) (HCNN) is a compound of formula IIa or IIb:

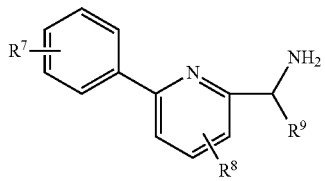
(IIa)

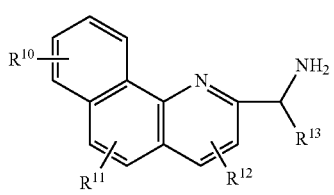
(IIb)

(III) (CNN) is a ligand of formula IIc or IId:

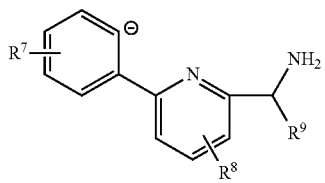
(IIc)

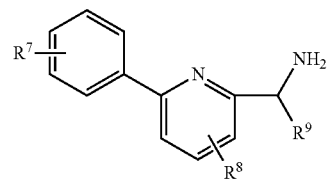
(IId)

wherein $R^1$-$R^{13}$ are, each independently, H, a C1-C20 aliphatic group, or a C5-C20 aromatic group; and (V) HCP is a compound of formula (IVa) and CP is a ligand of formula (IVb):

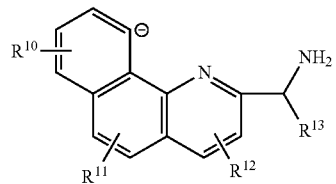
(IVa)

(IVb)

wherein, $R^{21}$-$R^{23}$ are, each independently, H, a C1-C20 aliphatic group, or a C5-C20 aromatic group;

provided that when M is Ru and

X=Y=Cl, $R^{23}$ is not hydrogen in the hexacoordinate complex of formula (VIII);

and when M is Ru and X=Cl, HCP is not (2,6-dimethylphenyl) diphenylphosphine (Hdmpp) and CP is not the anion of (2,6-dimethylphenyl) diphenylphosphine (dmpp) in the hexacoordinate complex of formula (IX).

2. A process for preparing the hexacoordinate complex of claim 1, comprising:

(i) reacting a compound of formula MX₂Y with HCOOH, thereby obtaining an intermediate compound of formula [MXY(CO)₂]ₙ;

(ii) reacting the intermediate compound of formula [MXY(CO)₂]ₙ with at least one ligand that is:

a (HCNN) compound of formula IIa or IIb:

(IIa)

-continued (IIb)

[Structure: R¹⁰-substituted benzoquinoline with NH₂ and R¹³ substituents; R¹¹ and R¹² substituents]

or a HCP compound of formula (Iva):

(IVa)

[Structure: benzene ring with H₃C, ²¹R²²RP, and R²³ substituents]

wherein:

$R^7$-$R^{13}$ and $R^{21}$-$R^{23}$ are, each independently, H, a C1-C20 aliphatic group, or a C5-C20 aromatic group;

in the presence of a solvent and optionally a tertiary amine of formula $N(R^{24}R_{25}R_{26})$, wherein $R^{24}$, $R^{25}$ and $R^{26}$ are, each independently, a C1-C6 aliphatic group; and (iii) optionally reacting the compound obtained in step (ii) with a basic compound that is potassium carbonate, calcium carbonate, or a mixture thereof and/or a nitrogen-containing (NN) compound of formula Ia, Ib, or Ic:

(Ia)

[Structure: H₂N-CR¹-CR²-NH₂]

(Ib)

[Structure: pyridine with NH₂, R³, R⁴ substituents]

(Ic)

[Structure: bipyridine with R⁵ and R⁶ substituents]

wherein, $R^1$-$R^6$ are, each independently, H, C1-C20 aliphatic group, or a C5-C20 aromatic group.

3. The process according to claim 2, wherein the hexacoordinate complex of formula (VI) is prepared and the process comprises:

(i) reacting a compound of formula $MX_2Y$ with HCOOH, thereby obtaining an intermediate compound of formula $[MXY(CO)_2]_n$;

(ii) reacting the compound of formula $[MXY(CO)_2]_n$ with a (HCNN) compound of formula IIa or IIb:

(IIa)

[Structure: R²-substituted phenyl-pyridine with NH₂, R³, R⁴ substituents]

(IIb)

[Structure: R¹⁰-substituted benzoquinoline with NH₂, R¹¹, R¹², R¹³ substituents]

wherein $R^7$-$R^{13}$ are, each independently, H, a C1-C20 aliphatic group, or C5-C20 aromatic group, in the presence of a solvent and a tertiary amine of formula $N(R^{24}R^{25}R^{26})$, wherein $R^{24}$, $R^{25}$ and $R^{26}$ are, each independently, a C1-C6 aliphatic group; and (iii) reacting the compound obtained in step (ii) with a basic compound that is potassium carbonate, calcium carbonate, or a and mixture thereof.

4. The process of claim 2, wherein the hexacoordinate complex of formula (VII) is obtained and the process comprises:

(i) reacting a compound of formula $MX_2Y$ with HCOOH, thereby obtaining an intermediate compound of formula $[MXY(CO)_2]_n$;

(ii) reacting the compound of formula $[MXY(CO)_2]_n$ with a (HCP) compound of formula (Iva):

(IVa)

[Structure: benzene ring with H₃C, ²¹R²²RP, and R²³ substituents]

wherein, $R^{21}$-$R^{23}$ are, each independently, H, a C1-C20 aliphatic group, or C5-C20 aromatic group in the presence of a solvent and a tertiary amine of formula $N(R^{24}R^{25}R^{26})$, wherein $R^{24}$, $R^{25}$ and $R^{26}$ are, each independently, a C1-C6 aliphatic group; and (iii) reacting the compound obtained in step (ii) with a basic compound that is potassium carbonate, calcium carbonate, or a mixture thereof and a nitrogen-containing (NN) compound of formula Ia Ib, or Ic:

(Ia)

[Structure: H₂N-CR¹-CR²-NH₂]

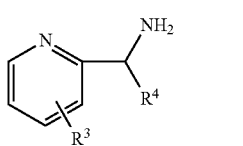
(Ib)

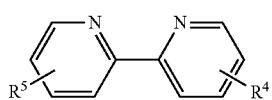
(Ic)

wherein, $R^1$-$R^6$ are, each independently, H, a C1-C20 aliphatic group, or a C5-C20 aromatic group.

5. The process of claim 2, wherein the hexacoordinate complex of formula (VIII) is obtained and the process comprises:
(i) reacting a compound of formula $MX_2Y$ with HCOOH, thereby obtaining an intermediate compound of formula $[MXY(CO)_2]_n$;
(ii) reacting the compound of formula $[MXY(CO)_2]_n$ with at least one (HCP) compound of formula (IVa) in the presence of a solvent:

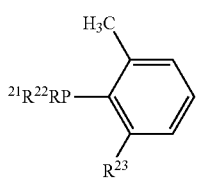
(IVa)

wherein, $R^{21}$-$R^{23}$ are, each independently, H, a C1-C20 aliphatic group, or C5-C20 aromatic group.

6. The process of claim 2, wherein the hexacoordinate complex of formula (IX) is obtained and the process comprises:
(i) reacting a compound of formula $MX_2Y$ with HCOOH, thereby obtaining an intermediate compound of formula $[MXY(CO)_2]_n$;
(ii) reacting the compound of formula $[MXY(CO)_2]_n$ with at least one (HCP) compound of formula (IVa):

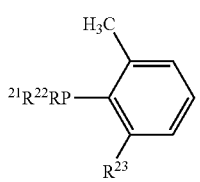
(IVa)

wherein, $R^{21}$-$R^{23}$ are, each independently, H, a C1-C20 aliphatic group, or a C5-C20 aromatic group,
in the presence of a solvent and of a tertiary amine of formula $N(R^{24}R^{25}R^{26})$, wherein $R^{24}$, $R^{25}$ and $R^{26}$ are, each independently, a C1-C6 aliphatic group, thereby obtaining a pentacoordinate complex;
(iii) reacting the pentacoordinate complex of step (ii) with carbon monoxide in the presence of a solvent.

7. The process of claim 6, wherein the solvent is $CH_2Cl_2$.

8. The process of claim 2, wherein the hexacoordinate complex of formula (V) is prepared and the process comprises:

(i) reacting a compound of formula $MX_2Y$ with HCOOH, thereby obtaining an intermediate compound of formula $[MXY(CO)_2]_n$;
(ii) reacting the compound of formula $[MXY(CO)_2]_n$ with a (HCNN) compound of formula IIa or IIb in the presence of a solvent:

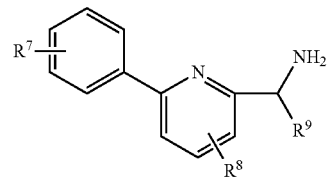
(IIa)

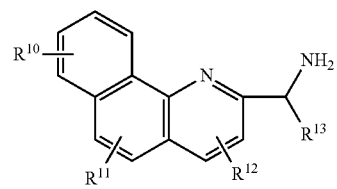
(IIb)

wherein, $R^7$-$R^{13}$ are, each independently, H, C1-C20 aliphatic group, or a C5-C20 aromatic group.

9. A method of preparing an alcohol, comprising reducing a ketone or aldehyde using transfer hydrogenation or hydrogenation with molecular hydrogen and the hexacoordinate complex of claim 1.

10. A process for reducing a ketone or aldehyde to the corresponding alcohol, comprising the steps:
(a) mixing a catalyst or pre-catalyst with a solution comprising at least one base and at least one substrate that is a C3-C42 ketone or a C2-C41 aldehyde, thereby obtaining a mixture; and
(b) contacting said mixture with molecular hydrogen or with at least one hydrogen-donor wherein the catalyst or pre-catalyst is the hexacoordinate complex of claim 1.

11. The process according to claim 10, comprising the steps:
(a) mixing a pre-catalyst complex of formula (2) with a solution comprising:
at least one base and at least one substrate that is a C3-C42 ketone or a C2-C41 aldehyde; and
at least one nitrogen-containing compound L that is:
(I) a NN compound of formula Ia, Ib, or Ic:

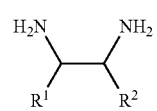
(Ia)

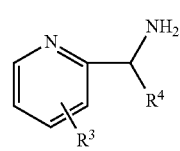
(Ib)

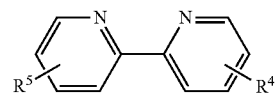
(Ic)

(II) a HCNN compound of formula IIa or IIb:

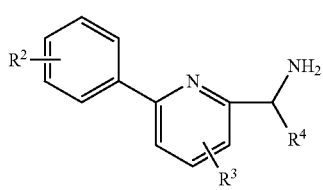
(IIa)

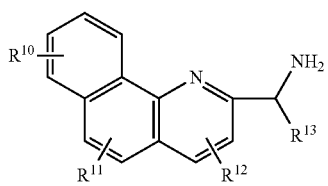
(IIb)

wherein, $R^1$-$R^{13}$ are, each independently, H, a C1-C20 aliphatic group, or a C5-C20 aromatic group, thereby obtaining a mixture; and (b) contacting said mixture with molecular hydrogen or with at least one hydrogen donor, wherein said pre-catalyst has formula (2):

$$MX_aY_b(CO)_2L'_d \quad (2)$$

wherein:
M is Ru or Os;
X and Y are, each independently, a halide, hydride, a C1-C20 carboxylate, or a C1-C20 alkoxide;
a and b are, independently, 0 or 1;
d is 1 or 2;
L' is at least one phosphorus-containing ligand that is a HCP compound of formula (IVa) or a CP ligand of formula (IVb):

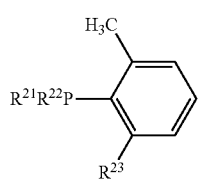
(IVa)

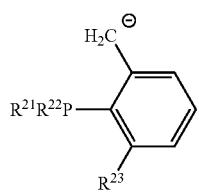
(IVb)

wherein, $R^{21}$-$R^{23}$ are, each independently, H, a C1-C20 aliphatic group, or a C5-C20 aromatic group,
provided that when M is Ru and a=1; b=0; d=2 and X=Cl, HCP is not (2,6-dimethylphenyl) diphenylphosphine and CP is not the anion of (2,6-dimethylphenyl) diphenylphosphine.

12. The process of claim 11, wherein the at least one hydrogen-donor is 2-propanol, sodium formate, ammonium formate, or a mixture of formic acid and trimethylamine.

13. The process of claim 10, comprising the steps:
(a) mixing a pre-catalyst complex of formula (3) with a solution comprising:
at least one base and at least one substrate that is a C3-C42 ketone or a C2-C41 aldehyde and
at least one phosphorus-containing compound L' that is:
(i) a phosphine (P) that is
a phosphine of formula $PR^{16}R^{17}R^{18}$, wherein $R^{16}$-$R^{18}$ are, each independently, H, a C1-C20 aliphatic group, or a C5-C20 aromatic group;
an optically active phosphine that is (S)-neomenthyldiphenylphosphine or (R)-(+)-2-(diphenylphosphino)-2'-methoxy-1,1'-binaphthyl;
(ii) a diphosphine (PP) that is:
a diphosphine of formula $P(R^{19})_2$—Z—$P(R^{20})_2$, wherein Z is a C2-C4 hydrocarbon chain or ferrocene optionally substituted with at least one C1-C20 aliphatic group, and $R^{19}$ and $R^{20}$ are, each independently, a C1-C20 aliphatic group or C5-C20 aromatic group;
an optically active diphosphine that is (R)-(6,6'-dimethoxybiphenyl-2,2'-diyl)bis(diphenylphosphine], (R)-(1,1'-binaphthalene-2,2'-diyl)bis(diphenylphosphine), (R)-(1,1'-binaphthalene-2,2'-diyl)bis[bis(3,5-dimethylmethyl)phosphine], (R)-1-{-2-[diphenylphosphine]ferrocenyl}ethyldicyclohexyl phosphine, (R)-1-{-2[bis(3,5-dimethyl-4-methoxyphenyl)phosphine]ferrocenyl}ethyldicyclohexyl phosphine or (2R,4R)-2,4-bis(diphenylphosphine)pentane, thereby obtaining a mixture; and
(b) contacting said mixture with molecular hydrogen or with at least one hydrogen-donor, wherein said pre-catalyst has formula (3)

$$MXY_b(CO)_2L \quad (3)$$

wherein:
M is Ru or Os;
X and Y are, each independently, a halide, hydride, a C1-C20 carboxylate, or C1-C20 alkoxide;
B is 0 or 1;
L is a nitrogen-containing ligand that is:
(I) a (NN) compound of formula Ia, Ib or Ic:

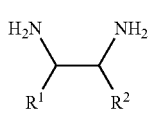
(Ia)

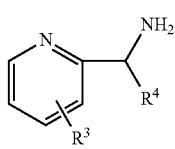
(Ib)

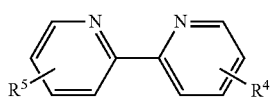
(Ic)

(II) a (HCNN) compound of formula IIa or IIb:

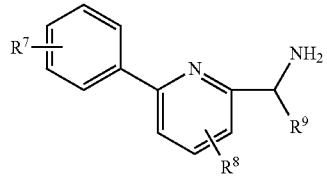
(IIa)

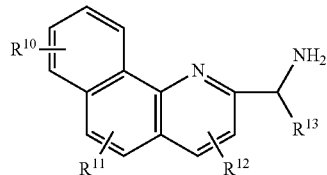
(IIb)

(III) a (CNN) ligand of formula IIc or IId:

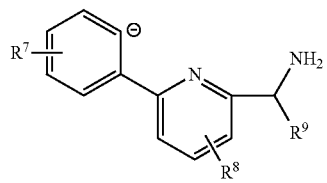
(IIc)

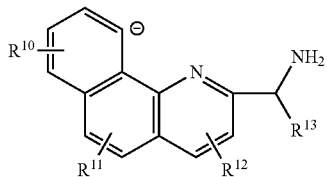
(IId)

wherein, $R^1$-$R^{13}$ are, each independently, H, a C1-C20 aliphatic group, or a C5-C20 aromatic group.

14. The process of claim 10, wherein in step (a) the base is an alkali metal alkoxide.

15. The process of claim 14, wherein the alkali metal alkoxide is sodium iso-propoxide, potassium tert-butoxide, potassium hydroxide, or potassium carbonate.

16. The process of claim 15, wherein the alkali metal alkoxide is potassium tert-butoxide.

17. The process of claim 10, wherein in step (a) the base is sodium iso-propoxide and in step (b) the mixture is contacted with at least one hydrogen donor.

18. The process of claim 10, wherein the molar ratio substrate/catalyst or pre-catalyst ranges from 1000/1 to 100000/1.

19. The process of claim 10, wherein the molar ratio substrate/base ranges from 20 to 50.

20. The process of claim 10, wherein the at least one hydrogen-donor is 2-propanol, sodium formate, ammonium formate, or a mixture of formic acid and trimethylamine.

* * * * *